(12) United States Patent
Ruan et al.

(10) Patent No.: US 7,947,875 B2
(45) Date of Patent: May 24, 2011

(54) METHODS AND MEANS FOR ALTERING FIBER CHARACTERISTICS IN FIBER-PRODUCING PLANTS

(75) Inventors: Yong Ling Ruan, Nicholls (AU); Robert T. Furbank, Wetangara (AU)

(73) Assignee: Commonwealth Scientific & Industrial Research Organisation, Campbell (AU)

(*) Notice: Subject to any disclaimer, the term of this patent is extended or adjusted under 35 U.S.C. 154(b) by 547 days.

(21) Appl. No.: 11/822,413

(22) Filed: Jul. 5, 2007

(65) Prior Publication Data
US 2008/0171391 A1 Jul. 17, 2008

Related U.S. Application Data

(63) Continuation of application No. 10/915,405, filed on Aug. 11, 2004, now abandoned.

(60) Provisional application No. 60/495,123, filed on Aug. 15, 2003.

(51) Int. Cl.
*C12N 15/82* (2006.01)
*A01H 5/00* (2006.01)
*A01H 5/10* (2006.01)

(52) U.S. Cl. ......... 800/290; 435/419; 800/284; 800/314

(58) Field of Classification Search ........................ None
See application file for complete search history.

(56) References Cited

U.S. PATENT DOCUMENTS
5,952,548 A 9/1999 Jin et al.
6,271,433 B1 8/2001 Keady et al.

FOREIGN PATENT DOCUMENTS
WO WO 01/17333 3/2001

OTHER PUBLICATIONS

Verma D.P.S. et al. Plant Callose synthase complexes. Plant Molecular Biology 47: 693-701, 2001.*
Doerks T. et al. Protein annotation: detective work for function prediction. Trends Genet. Jun. 1998;14(6):248-50.*
Kaye C. et al. Characterization of a gene for spinach CAP160 and expression of two spinach cold-acclimation proteins in tobacco. Plant Physiol. Apr. 1998;116(4):1367-77.*
Whisstock J.C. et al. Prediction of protein function from protein sequence and structure. Q Rev Biophys. Aug. 2003;36(3):307-40. Review.*
Genbank Accession AF085717, Apr. 20, 1999, *Gossypium hirsutum* putative callose synthase catalytic subunit (CFL1) mRNA, complete cds.*
Genbank Accession AAD25952, Apr. 20, 1999, putative callose synthase catalytic subunit [*Gossypium hirsutum*].*
Amor Y. et al. "A Membrane-associated form of sucrose synthase and its potential role in Synthesis of cellulose and callose in plants" Proc. Natl. Acad. Sci. USA, 1995, pp. 9353-9357, vol. 92, Plant Biology.

Baluška F. et al."Maize calreticulin localizes preferentially to plasmodesmata in root apex" The Plant Journal, 1999, vol. 19, No. 4, pp. 481-488.
Bucher et al. "Local Expression of Enzymatically active class I β-1, 3-glucanase Enhances Symptoms of TMV infection in Tobacco" The Plant Journal, 2001, vol. 28, No. 3, pp. 361-369.
Cui et al. "A Putative Plant Homolog of the Yeast β-1,3-glucan Synthase Subunit *FKS1* from cotton (*Gossypium hirsutum* L.) Fibers" Planta, 2000, vol. 213, pp. 223-230.
Hong et al. "A Cell Plate-Specific Callose Synthase and Its Interaction with Phragmoplastin" The Plant cell, 2001, vol. 13, pp. 755-768.
Hudspeth et al. "Characterization and Expression of Chitinase and 1,3-β-Glucanase genes in Cotton" Plant Molecular Biology, 1996, vol. 31, pp. 911-916.
Kaye C. et al., "Characterization of a gene for spinach CAP160 and expression of two spinach cold-acclimation proteins in tobacco", *Plant Physiol*, 1998, pp. 1367-1377, vol. 116(4), Lancaster, PA.
Kim et al., "Cotton Fiber Growth in Planta and in Vitro. Models for Plant Cell Elongation and Cell Wall Biogenesis", *Plant Physiology*, 2001, pp. 1361-1366, vol. 127, American Society of Plant Physiologists, Rockville, Maryland, U.S.
Pillonel et al., "Influence of external factors on callose and cellulose synthesis during incubation in vitro of intact cotton fibres with [14C]sucrose" *Planta*, 1985, pp. 76-84, vol. 165, Springer-Verlag.
Ruan et al., "The Control of Single-Celled Cotton Fiber Elongation by Developmentally Reversible Gating of Plasmodesmata and Coordinated Experession of Sucrose and K+ Transporters and Expansin," *The Plant Cell*, 2001, pp. 47-60, vol. 13, American Scoeity of Plant Physiologists, Rockville, Maryland, U.S.
Shimizu et al., "Changes in Levels of mRNAs for Cell WII-Related Enzymes in Growing Cotton Fiber Cells," *Plant Cell Physiol*, 1997, pp. 375-378, vol. 38, No. 3, Japanese Society of Plant Physiologists, Kyoto, Japan.
Shimizu et al.,"PIR Sequence database posting. Accession No. T09872", 1999.
Shimizu Y. et al. "Genbank accession No. D88416, Cotton mRNA for endo-1,3-beta-glucenase, clone CF922", 1997, Partial CDs.
Supplementary European Search Report dated Jun. 20, 2007.
Temple S.J. et al., "Down-regulation of specific members of the glutamine synthetase gene family in alfalfa by antisense RNA technology", *Plant Mol Biol*. 1998, pp. 535-547, vol. 37(3), Dordrecht, Holland.
Whisstock J.C. et al. "Prediction of protein function from protein sequence and structure",. *Q Rev Biophys*, 2003, pp. 307-340, vol. 36(3) Review.
Waterhouse et al,"Virus resistance and gene silencing: killing the messenger", *Trends Plant Sci*, 1999, pp. 452-457, vol. 4(11).
Waterkeyn, "Cytochemical Localization and Function of the 3-Linked Glucan Callose in the Developing Cotton Fibre Cell Wall", *Protoplasma*, 1981, pp. 49-67, vol. 106, Springer-Verlag.

* cited by examiner

*Primary Examiner* — Cynthia Collins
(74) *Attorney, Agent, or Firm* — Buchanan Ingersoll & Rooney PC (57) ABSTRACT

Methods and means are provided for modulating fiber length in fiber producing plants such as cotton by altering the fiber elongation phase. The fiber elongation phase may be increased or decreased by interfering with callose deposition in plasmodesmata at the base of the fiber cells.

14 Claims, 3 Drawing Sheets

METHODS AND MEANS FOR ALTERING FIBER CHARACTERISTICS IN FIBER-PRODUCING PLANTS

FIELD OF THE INVENTION

The invention relates to the field of agriculture, more specifically towards the use of molecular biology techniques to alter fiber producing plants, particularly cotton plants and/or accelerate breeding of such fiber containing plants. Methods and means are provided to increase fiber length, particularly lint fiber length or to decrease the length of fuzz fibers. Methods are also provided to identify molecular markers associated with fiber length in a population of cotton varieties and related progenitor plants.

BACKGROUND ART

Much of the high quality fiber for the textile industry is provided for by cotton. About 90% of cotton grown worldwide is *Gossypium hirsutum* L., whereas *Gossypium barbadense* accounts for about 8%. Consequently, the modification of cotton fibers characteristics to better suit the requirements of the industry is a major effort in breeding by either classical methods or by genetically altering the genome of cotton plants. Goals to be achieved include increased lint fiber length, strength, dyability decreased fuzz fiber production, fiber maturity ratio, immature fiber content, fiber uniformity and micronaire.

WO024585 describes methods and means to modulate fiber quality in fiber-producing plants, such as cotton, by modulating sucrose synthase activity and/or expression in such plants.

U.S. Pat. No. 6,472,588 and WO0117333 provides methods for increasing the quality of cotton fiber produced from a cotton plant by transformation with a DNA encoding sucrose phosphate synthase. The fiber qualities include strength, length, fiber maturity ratio, immature fiber content, fiber uniformity and micronaire.

WO9508914 discloses a fiber producing plant comprising in its genome a heterologous genetic construct. The genetic construct comprises a fiber-specific promoter and a coding sequence encoding a plant peroxidase, such as a cotton peroxidase.

WO9626639 provides methods whereby encoding sequence preferentially directing gene expression in ovary tissue, particularly very early in fruit development, are utilized to express plant growth modifying hormones in cotton ovule tissue. The methods permit the modification of the characteristics of boll set in cotton plants and provide a mechanism for altering fiber quality characteristics such as fiber dimension and strength.

U.S. Pat. No. 5,981,834, U.S. Pat. No. 5,597,718, U.S. Pat. No. 5,620,882, U.S. Pat. No. 5,521,708 and U.S. Pat. No. 5,495,070 all disclose a method for genetically engineering a fiber-producing plant and the identification of cDNA clones useful for identifying fiber genes in cotton. The cDNA clones are useful in developing corresponding genomic clones from fiber producing plants to enable genetic engineering of cotton and other plants using these genes. Coding sequence from these isolated genes are used in sense or antisense orientation to alter the fiber characteristics of transgenic fiber producing plants.

Published US patent applications US2002049999 and US2003074697 both disclose cotton plants of the genus *Gossypium* with improved cotton fiber characteristics. The cotton plant has an expression cassette containing a gene coding for an enzyme selected from the group consisting of endoxyloglucan transferase, catalase and peroxidase so that the gene is expressed in cotton fiber cells to improve the cotton fiber characteristics.

U.S. Pat. No. 5,880,110 produces cotton fibers with improved fiber characteristics by treatment with brassinosteroids.

WO 01/40250 provides methods for improving cotton fiber quality by modulating transcription factor gene expression.

WO 96/40924 provides novel DNA constructs which may be used as molecular probes or inserted into a plant host to provide for modification of transcription of a DNA sequence of interest during various stages of cotton fiber development. The DNA constructs comprise a cotton fiber transcriptional initiation regulatory region associated with a gene, which is expressed in cotton fiber. Also is novel cotton having a cotton fiber, which has a natural color, introduced by the expression in cotton fiber cell, using such a construct, of pigment genes.

EP0834566 provides a gene which controls the fiber formation mechanism in cotton plant and which can be used for industrially useful improvement.

However, there is still need for alternative methods and means to alter fiber characteristics of fiber-producing plants such as cotton, which may be further combined with any of other methods to alter fiber characteristics. Such a method is described in the embodiments and paragraphs described hereinafter.

SUMMARY OF THE INVENTION

In one embodiment of the invention a method for modifying a fiber of a fiber-producing plant, such as cotton, is provided comprising the step of altering a fiber cell elongation phase by modulating deposition of callose at the neck of the plasmodesmata at the base of the fiber cell.

In another embodiment of the invention a method for increasing the length of a fiber of a fiber producing plant, such as cotton is provided, comprising the step of introducing a chimeric gene into a cell of the fiber producing plant, wherein the chimeric gene, when expressed in the cell of the fiber-producing plant increases the fiber elongation phase and increases the deposition of callose. The chimeric gene may comprise the following operably linked DNA elements:

- a plant expressible promoter, preferably a plant expressible promoter which controls transcription preferentially in the fiber cells such as a fiber-specific beta tubulin promoter from cotton, a fiber-specific actin promoter from cotton, a fiber specific promoter from a lipid transfer protein gene from cotton, a promoter from an expansin gene from cotton or a promoter from a chitinase gene in cotton;
- a transcribed DNA region, which when transcribed yields a double-stranded RNA molecule capable of reducing the expression of a gene endogenous to the fiber producing plant, the gene being involved in callose removal from the plasmodesmata, such as a 1,3-β-glucanase gene which is expressed at the base of the fiber cell, at the end of the fiber elongation phase in the fiber producing plant, and the RNA molecule comprising a first and second RNA region wherein
  - the first RNA region comprises a nucleotide sequence of at least 19 consecutive nucleotides having at least about 94% sequence identity to the nucleotide sequence of the endogenous gene;
  - the second RNA region comprises a nucleotide sequence complementary to the 19 consecutive nucleotides of the first RNA region;

the first and second RNA region are capable of base-pairing to form a double stranded RNA molecule between at least the 19 consecutive nucleotides of the first and second region; and a 3' end region comprising transcription termination and polyadenylation signals functioning in cells of the plant.

The endogenous gene may encode a protein comprising the amino acid sequence of SEQ ID 4 or it may comprise the nucleotide sequence of SEQ ID No 1 or the first RNA region may comprise a nucleotide sequence of at least 19 consecutive nucleotides having at least about 94% sequence identity to the nucleotide sequence of SEQ ID No 1.

In another embodiment of the invention the chimeric gene may comprise a plant-expressible promoter, preferably a plant-expressible promoter which controls transcription preferentially in the fiber cells, such as a fiber-specific beta tubulin promoter from cotton, a fiber-specific actin promoter from cotton, a fiber specific promoter from a lipid transfer protein gene from cotton, a promoter from an expansin gene from cotton or a promoter from a chitinase gene in cotton;

a DNA region encoding a β-1,3 glucan synthase protein, such as a DNA region comprising the nucleotide sequence of SEQ ID No 2; and a 3'end region comprising transcription termination and polyadenylation signals functioning in cells of the plant.

In yet another embodiment of the invention, a method for decreasing the length of a fiber of a fiber producing plant, comprising the step of introducing a chimeric gene into a cell of the fiber producing plant, wherein the chimeric gene, when expressed in the cell of the fiber-producing plant decreases the deposition of callose and decreases the fiber elongation phase.

It is also an object of the invention to provide a method for identifying allelic variations of the genes encoding proteins involved in fiber elongation in a population of different genotypes, cultivars or varieties of a particular plant species, preferably a fiber-producing plant species, which are correlated either alone or in combination with the length of fibers produced, comprising the steps of (a) Providing a population of different varieties or genotypes of a particular plant species or interbreeding plant species comprising different allelic forms of the nucleotide sequences encoding callose synthase or β-1,3 glucanase, particularly of SEQ ID No 1 or SEQ ID 2;

(b) Determining parameters related to fiber length for each individual of the population;

(c) Determining the presence of a particular allelic form of the nucleotide sequences encoding callose synthase or β-1,3 glucanase, particularly of SEQ ID No 1 or SEQ ID 2;

(d) Correlating the occurrence of particular fiber length with the presence of a particular allelic form of the mentioned nucleotide sequence or a particular combination of such allelic forms.

In yet another embodiment, the invention provides the chimeric genes as herein described, as well as cells of a fiber producing plant comprising such chimeric genes. It is also an objection of the invention to provide fiber-producing plants, such as cotton, and seeds or progeny comprising a chimeric gene according to the invention, particularly fiber producing plants which have increased fiber length or increased drought resistance.

The invention also provides fibers produced according to the methods of the invention.

DETAILED DESCRIPTION OF DIFFERENT EMBODIMENTS

Each cotton lint fiber is a single cell that elongates to 2.5 to 3.0 cm form the seed coat epidermis within ~16 days after anthesis (DAA). Ruan et al. 2001 (The Plant Cell 13: pp 47-60) found that this elongation process was controlled by gating of the plasmodesmata and coordinated expression of sucrose and K+ transporters and expansin. Single celled cotton fibers interconnect with the underlying seed coat only at their base regions, where a high number of plasmodesmata are present. Plasmodesmata are the intercellular cytoplasmic connections that act as gates controlling molecular trafficking from cell to cell. During the rapid elongation phase (~10 to ~16 DAA), the symplastic connection was disrupted, allowing the rapid build-up of a turgor in the fiber cell, which is higher than in the underlying seed coat cells, by active solute import into the fiber cell. Coordinated with the cell wall loosening (inter alia by expansins), this higher turgor pushes out the fiber cell to its length. Ruan et al. also examined the possibility that callose deposition at the neck region of the plasmodesmata was implicated in the closing thereof, but found no correlation using a monoclonal antibody against callose, between the deposit of callose and the closing and reopening of the plasmodesmata.

The current invention is based on the observations by the inventors on the one hand, that the length of the period of the closing of plasmodesmata in different cotton cultivars is correlated with the variation in fiber length, and on the other hand, that callose deposition is involved in the closure of the plasmodesmata. Additionally, it was observed that the timing and the level of expression of a fiber-specific β-1,3-glucanase gene among three cotton cultivars differing in fiber length correlated with the degradation of callose in the plasmodesmata.

Thus, in one embodiment of the invention, a method is provided for altering the length of a fiber of a fiber-producing plant, such as a cotton plant, comprising the step of altering the fiber cell elongation phase by modulating the deposition of callose at the neck of the plasmodesmata at the base of the fiber cell.

Conveniently, the deposition of callose may be altered by introduction of a chimeric gene capable of modulating the deposition of callose at the neck of the plasmodesmata at the base of the fiber cell. This may be achieved e.g. by increasing the expression level and/or the activity of the encoded product of a gene involved in callose removal, such as a β-1,3 glucanase. Deposition of callose may also be altered by increasing the expression level and/or the activity of the encoded product of a gene involved in callose synthesis and accumulation, such as a β-1,3 glucan synthase (callose synthase).

In one embodiment, the chimeric gene may encode a silencing RNA molecule or an inhibitory RNA molecule, capable of reducing the expression of a gene involved in callose removal from the plasmodesmata at the base of the fiber cell to increase the fiber length. Such reduction of the expression of a gene involved in callose removal should occur preferably through post-transcriptional silencing. However, it will be clear that even when an inhibitory RNA molecule decreases the expression of a gene involved in callose removal through post-transcriptional silencing, such an RNA molecule may also exert other functions within a cell, such as guiding DNA methylation of the endogenous gene involved in callose removal, again ultimately leading to decreased expression of that gene. Also, expression of endogenous genes involved in callose removal may be reduced by transcriptional silencing, e.g. by using RNAi or dsRNA targeted against the promoter region of the endogenous gene involved in callose removal.

Several methods are available in the art to produce a silencing RNA molecule, i.e. an RNA molecule which when expressed reduces the expression of a particular gene or group of genes, including the so-called "sense" or "antisense" RNA technologies.

Thus in one embodiment, the inhibitory RNA molecule encoding chimeric gene is based on the so-called antisense technology. In other words, the coding region of the chimeric gene comprises a nucleotide sequence of at least 20 consecutive nucleotides of the complement of the nucleotide sequence of the endogenous gene involved in callose removal of the plant. Such a chimeric gene may be constructed by operably linking a DNA fragment comprising at least 20 nucleotides from a gene involved in callose removal, isolated or identified as described elsewhere in this application, in inverse orientation to a plant expressible promoter and 3' end formation region involved in transcription termination and polyadenylation. It will be clear that there is no need to know the exact nucleotide sequence or the complete nucleotide sequence of such a DNA fragment from the isolated gene involved in callose removal.

In another embodiment, the inhibitory RNA molecule encoding chimeric gene is based on the so-called co-suppression technology. In other words, the coding region of the chimeric gene comprises a nucleotide sequence of at least 20 consecutive nucleotides of the nucleotide sequence of the endogenous gene involved in callose removal of the plant. Such a chimeric gene may be constructed by operably linking a DNA fragment comprising at least 20 nucleotides from a gene involved in callose removal, isolated or identified as described elsewhere in this application, in direct orientation to a plant expressible promoter and 3' end formation region involved in transcription termination and polyadenylation. Again, it will be clear that there is no need to know the exact nucleotide sequence or the complete nucleotide sequence of such a DNA fragment from the isolated gene involved in callose removal.

The efficiency of the above mentioned chimeric genes in reducing the expression of the endogenous gene involved in callose removal may be further enhanced by the inclusion of DNA element which result in the expression of aberrant, unpolyadenylated inhibitory RNA molecules or results in the retention of the inhibitory RNA molecules in the nucleus of the cells. One such DNA element suitable for that purpose is a DNA region encoding a self-splicing ribozyme, as described in WO 00/01133 (incorporated by reference). Another such DNA element suitable for that purpose is a DNA region encoding an RNA nuclear localization or retention signal, as described in PCT/AU03/00292 (incorporated by reference).

A convenient and very efficient way of downregulating the expression of a gene of interest uses so-called double-stranded RNA (dsRNA) or interfering RNA (RNAi), as described e.g. in WO99/53050 (incorporated by reference). In this technology, an RNA molecule is introduced into a plant cell, whereby the RNA molecule is capable of forming a double stranded RNA region over at least about 19 to about 21 nucleotides, and whereby one of the strands of this double stranded RNA region is about identical in nucleotide sequence to the target gene ("sense region"), whereas the other strand is about identical in nucleotide sequence to the complement of the target gene or of the sense region ("antisense region"). It is expected that for silencing of the target gene expression, the nucleotide sequence of the 19 consecutive nucleotide sequences may have one mismatch, or the sense and antisense region may differ in one nucleotide. To achieve the construction of such RNA molecules or the encoding chimeric genes, use can be made of the vector as described in WO 02/059294.

Thus, in one embodiment of the invention, a method for increasing the length of a fiber of a fiber producing plant, such as cotton, is provided comprising the step of introducing a chimeric gene into a cell of the fiber producing plant, wherein the chimeric gene comprises the following operably linked DNA elements:

(e) a plant expressible promoter, preferably a plant expressible promoter which controls transcription preferentially in the fiber cells;

(f) a transcribed DNA region, which when transcribed yields a double-stranded RNA molecule capable of reducing the expression of a gene endogenous to the fiber producing plant, the gene being involved in callose removal from the plasmodesmata, and the RNA molecule comprising a first and second RNA region wherein
  i) the first RNA region comprises a nucleotide sequence of at least 19 consecutive nucleotides having at least about 94% sequence identity to the nucleotide sequence of the endogenous gene;
  ii) the second RNA region comprises a nucleotide sequence complementary to the at least 19 consecutive nucleotides of the first RNA region;
  iii) the first and second RNA region are capable of base-pairing to form a double stranded RNA molecule between at least the 19 consecutive nucleotides of the first and second region; and (g) a 3' end region comprising transcription termination and polyadenylation signals functioning in cells of the plant.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region, which is functionally or structurally defined, may comprise additional DNA regions etc.

The length of the first or second RNA region (sense or antisense region) may vary from about 19 nucleotides (nt) up to a length equaling the length (in nucleotides) of the endogenous gene involved in callose removal. The total length of the sense or antisense nucleotide sequence may thus be at least at least 25 nt, or at least about 50 nt, or at least about 100 nt, or at least about 150 nt, or at least about 200 nt, or at least about 500 nt. It is expected that there is no upper limit to the total length of the sense or the antisense nucleotide sequence. However for practical reason (such as e.g. stability of the chimeric genes) it is expected that the length of the sense or antisense nucleotide sequence should not exceed 5000 nt, particularly should not exceed 2500 nt and could be limited to about 1000 nt.

It will be appreciated that the longer the total length of the sense or antisense region, the less stringent the requirements for sequence identity between these regions and the corresponding sequence in the endogenous gene involved in callose removal or its complement. Preferably, the nucleic acid of interest should have a sequence identity of at least about 75% with the corresponding target sequence, particularly at least about 80%, more particularly at least about 85%, quite particularly about 90%, especially about 95%, more especially about 100%, quite especially be identical to the corresponding part of the target sequence or its complement. However, it is preferred that the nucleic acid of interest always includes a sequence of about 19 consecutive nucleotides, particularly about 25 nt, more particularly about 50 nt, especially about 100 nt, quite especially about 150 nt with 100% sequence identity to the corresponding part of the target nucleic acid. Preferably, for calculating the sequence identity and designing the corresponding sense or antisense sequence, the number of gaps should be minimized, particularly for the shorter sense sequences.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other, is regarded as a position with non-identical residues. The alignment of the two sequences is performed by the Needleman and Wunsch algorithm (Needleman and Wunsch 1970). The computer-assisted sequence alignment above, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

dsRNA encoding chimeric genes according to the invention may comprise an intron, such as a heterologous intron, located e.g. in the spacer sequence between the sense and antisense RNA regions in accordance with the disclosure of WO 99/53050 (incorporated herein by reference).

As used herein, an "endogenous gene involved in callose removal" is a gene whose expression product regulates or catalyzes the breakdown of callose deposited at a particular location in plants. "Callose" is a long-chain carbohydrate polymer, consisting of β-1,3-glucan, that seals certain regions, e.g., damaged sieve elements, growing pollen tubes, or plasmodesmata.

As used herein, an "endogenous gene" is a gene that naturally occurs in the species of the fiber-producing plant that has been chosen for modulation of fiber characteristics, or a gene that occurs naturally in a species of another fiber-producing plant but may be introduced into the species of the fiber-producing plant that has been chosen for modulation of fiber characteristics, by conventional breeding techniques.

A target gene involved in callose removal from plasmodesmata at the base of fiber cells in fiber-producing plants such as cotton, is an endo-1,3-β-glucanase gene that is naturally expressed at the base of the fiber cell, at the end of fiber elongation phase. An example of such a 1,3-β-glucanase gene from cotton, is a gene encoding a protein comprising the amino acid sequence of SEQ ID No 4 or comprising the nucleotide sequence of SEQ ID 1 (or Genbank Accession number D88416). Shimuzu et al. (Plant Cell Physiology 38 (3), pp 375-378, 1997) have described that the level of mRNA for endo-1,3-β-glucanase was very low in elongating fiber cells, but increased gradually at the onset of secondary wall synthesis, accompanying the massive deposition of cellulose, but characterized this endo-1,3-β-glucanase activity as required for the deposition of cellulose. The current invention has correlated the endo-1,3-β-glucanase activity with callose removal in different cotton variety with different lengths of fiber elongation phases.

Variants of the endo-1,3-β-glucanase gene involved in removal of callose from plasmodesmata at the base of elongating fiber cells, such as the endogenous genes coding for endo-1,3-β-glucanase from fiber producing plants different from cotton, may be found by stringent hybridization using the nucleotide sequence of SEQ ID No 1, or a part thereof comprising at least about 25 or 50 consecutive nucleotides of SEQ ID No 1 or the complementary nucleotide sequences thereof, as a probe.

"Stringent hybridization conditions" as used herein means that hybridization will generally occur if there is at least 95% and preferably at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared carrier DNA such as salmon sperm DNA, followed by washing the hybridization support in 0.1×SSC at approximately 65° C. Other hybridization and wash conditions are well known and are exemplified in Sambrook et al, Molecular Cloning: A Laboratory Manual, Second Edition, Cold Spring Harbor, N.Y. (1989), particularly chapter 11.

Such variant sequences may also be obtained by DNA amplification using oligonucleotides specific for endo-1,3-β-glucanase gene as primers, such as but not limited to oligonucleotides comprising about 20 to about 50 consecutive nucleotides of the nucleotide sequence of SEQ ID 1 or its complement. Variant sequences include modifications of a sequence by addition, deletion or substitution of nucleotides.

As used herein, the term "promoter" denotes any DNA which is recognized and bound (directly or indirectly) by a DNA-dependent RNA-polymerase during initiation of transcription. A promoter includes the transcription initiation site, and binding sites for transcription initiation factors and RNA polymerase, and can comprise various other sites (e.g., enhancers), at which gene expression regulatory proteins may bind.

As used herein, the term "plant-expressible promoter" means a DNA sequence which is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S, the subterranean clover virus promoter No 4 or No 7, or T-DNA gene promoters and the like.

A plant-expressible promoter that control initiation and maintenance of transcription preferentially in fiber cells is a promoter that drives transcription of the operably linked DNA region to a higher level in fiber cells and the underlying epidermis cells than in other cells or tissues of the plant. Such promoters include the promoter from cotton from a fiber-specific β-tubulin gene (as described in WO0210377), the promoter from cotton from a fiber-specific actin gene (as described in WO0210413), the promoter from a fiber specific lipid transfer protein gene from cotton (as described in U.S. Pat. No. 5,792,933), a promoter from an expansin gene from cotton (WO9830698) or a promoter from a chitinase gene in cotton (US2003106097) or the promoters of the fiber specific genes described in U.S. Pat. No. 6,259,003 or U.S. Pat. No. 6,166,294.

As mentioned above, deposition of callose, to increase the closing of the plasmodesmata at the base of the fiber cell and consequently increase the fiber elongation phase, may also be altered by increasing the expression level and/or the activity of the encoded product of a gene involved in callose synthesis and accumulation, such as a β-1,3 glucan synthase (callose synthase).

Thus in another embodiment, a method is provided to increase fiber length comprising introduction of a chimeric gene into cells of a fiber-producing plant of a chimeric gene comprising
- a plant-expressible promoter, preferably a plant-expressible promoter which controls transcription preferentially in the fiber cells;
- a DNA region encoding a β-1,3 glucan synthase protein; and
- a 3'end region comprising transcription termination and polyadenylation signals functioning in cells of the plant.

A suitable DNA region encoding a β-1,3 glucan synthase protein is a DNA region comprising the nucleotide sequence of SEQ ID No 2 (Genbank Accession number AI730469) or encoding a protein comprising the amino acid sequence of SEQ ID No 3.

Alternative DNA regions encoding a β-1,3 glucan synthase protein may be found in nucleotide sequence databases such as the entries with the following identification numbers AF085717 (*Gossypium hirsutum*) AY324384 (*Oryza sativa* (*japonica* cultivar-group); NM_179940, NM_121303, NM_116593, NM_179622, NM_123045, NM_116736, NM_115772, NM_112317, NM_111596, NM_100528, NM_100436 (*Arabidopsis thaliana*); AY177665 (*Hordeum vulgare* subsp. *vulgare*); BQ702515 (*Pinus taeda*); BQ696956, BG625796 BG625791, BG317521, BF516675 (*Pinus taeda*); CA935202 (*Glycine max*) CA900204, CA900203, CA900202 (*Phaseolus coccineus*); BI978498 (*Rosa chinensis*); BU964672, BU927399 (*Glycine max*); AL750522 (*Pinus pinaster*); BQ081239, BQ080234 (*Glycine max*); AJ430780 (*Vitis vinifera*); BM270236, BF066990, BG651282, BG509952, BG363511, BG359433, BG157340, BM086291 (*Glycine max*); AF237733 (*Arabidopsis thaliana*); BE644560 (*Suaeda maritima* subsp. *salsa*); BE040372 (*Oryza sativa*).

Variants of these sequences may be obtained by substitution, deletion or addition of particular nucleotides, and such variants may also be suitable for the currently described methods and means, particularly if they retain endo-β-1,3-glucan synthase activity.

It will be clear that the methods and means described herein to increase the length of fibers in fiber-producing plants may be combined with each other to further increase the length of fibers. The methods of the current application may of course also be combined with other methods to alter fiber characteristics as known in the art.

It is also expected that the methods described here to increase the fiber elongation phase and fiber length, particularly the reduction of expression of the endogenous gene involved in callose removal, will also lead to increased drought resistance, particularly of the fibers.

For some fiber-producing plants, it may sometimes be beneficial to decrease fiber length, particularly eliminate fiber production. This can be achieved according to the invention by shortening the fiber elongation phase through decreased callose deposition or increased callose removal. To this end, chimeric genes may be introduced which when expressed decrease callose deposition or increase callose removal. Such chimeric genes may comprise the following operably linked DNA fragments:
- a plant-expressible promoter, preferably a plant-expressible promoter which controls transcription preferentially in fiber cells;
- a DNA region encoding a gene involved in callose removal, such as a β-1,3 glucanase protein; and
- a 3'end region comprising transcription termination and polyadenylation signals functioning in cells of that plant;

or
- a plant expressible promoter which controls transcription preferentially in fiber cells;
- a transcribed DNA region, which when transcribed yields a double-stranded RNA molecule capable of reducing the expression of a gene endogenous to the fiber producing plant, the gene being involved in callose deposition, such as a callose synthase, in the plasmodesmata at the base of a fiber cell, and wherein the RNA molecule comprising a first and second RNA region wherein
  - the first RNA region comprises a nucleotide sequence of at least 19 consecutive nucleotides having at least about 94% sequence identity to the nucleotide sequence of the mentioned endogenous gene;
  - the second RNA region comprises a nucleotide sequence complementary to the 19 consecutive nucleotides of the first RNA region;
  - the first and second RNA region are capable of base-pairing to form a double stranded RNA molecule between at least the 19 consecutive nucleotides of the first and second region; and
- a 3' end region comprising transcription termination and polyadenylation signals functioning in cells of the fiber producing plant.

The invention also encompasses the chimeric genes herein described, as well as plants, seeds, tissues comprising these chimeric genes, and fibers produced from such plants.

Methods to transform plants are well known in the art. Methods to transform cotton plants are also well known in the art. Agrobacterium-mediated transformation of cotton has been described e.g. in U.S. Pat. No. 5,004,863 or in U.S. Pat. No. 6,483,013 and cotton transformation by particle bombardment is reported e.g. in WO 92/15675.

The chimeric genes may be introduced by transformation in cotton plants from which embryogenic callus can be derived, such as Coker 312, Coker 310, Coker 5Acala SJ-5, GSC25110, FiberMax 819, Siokra 1-3, T25, GSA75, Acala SJ2, Acala SJ4, Acala SJ5, Acala SJ-C1, Acala B1644, Acala B1654-26, Acala B1654-43, Acala B3991, Acala GC356, Acala GC510, Acala GAM1, Acala C1, Acala Royale, Acala Maxxa, Acala Prema, Acala B638, Acala B1810, Acala B2724, Acala B4894, Acala B5002, non Acala "picker" Siokra, "stripper" variety FC2017, Coker 315, STONEV-ILLE 506, STONEVILLE 825, DP50, DP61, DP90, DP77, DES119, McN235, HBX87, HBX191, HBX107, PC 3027, CHEMBRED A1, CHEMBRED A2, CHEMBRED A3, CHEMBRED A4, CHEMBRED B1, CHEMBRED B2, CHEMBRED B3, CHEMBRED C1, CHEMBRED C2, CHEMBRED C3, CHEMBRED C4, PAYMASTER 145, HS26, HS46, SICALA, PIMA S6 and ORO BLANCO PIMA and plants with genotypes derived thereof.

"Cotton" as used herein includes *Gossypium hirsutum*, *Gossypium barbadense*, *Gossypium arboreum* and *Gossypium herbaceum*.

Nevertheless, the methods and means of the current invention may also be employed for other plant species such as hemp, jute, flax and woody plants, including but not limited to *Pinus* spp., *Populus* spp., *Picea* spp., *Eucalyptus* spp. etc.

The obtained transformed plant can be used in a conventional breeding scheme to produce more transformed plants with the same characteristics or to introduce the chimeric gene according to the invention in other varieties of the same or related plant species, or in hybrid plants. Seeds obtained from the transformed plants contain the chimeric genes of the invention as a stable genomic insert and are also encompassed by the invention.

In another embodiment, a method for identifying allelic variations of the proteins involved in fiber length and/or drought resistance in a population of different genotypes or varieties of a particular plant species, preferably a fiber-producing plant species, which are correlated either alone or in combination with the quantity and/or quality of fiber production is provided. These method includes the following steps:
a) providing a population of different varieties or genotypes of a particular plant species or interbreeding plant species comprising different allelic forms of the nucleotide sequences encoding callose synthase or β-1,3-glucanase, such as nucleotide sequences comprising SEQ ID No 1 or 2. The different allelic forms may be identified using the methods described elsewhere in this application. Preferably, a segregating population is provided, wherein different combinations of the allelic variations of the proteins involved in callose deposition and/or fiber elongation or drought resistance are present. Methods to produce segregating populations are well known in the art of plant breeding;
b) determining parameters related to fiber length or callose deposition at the neck of the plasmodesmata at the base of the fiber cell during fiber elongation or drought resistance for each individual of the population;
c) determining the presence of a particular allelic form of the nucleotide sequences encoding β-1,3-glucanase or β-1,3-glucan synthase such as nucleotide sequences comprising SEQ ID No 1 or 2, for each individual of the population; and
d) correlating the occurrence of particular fiber length or callose deposition or drought resistance with the presence of a particular allelic form of the mentioned nucleotide sequence or a particular combination of such allelic forms.

The resulting information may be used to accelerate breeding program varieties with particular fiber or drought resistance characteristics, by determining the presence or absence of allelic forms, using conventional molecular biology techniques.

Biochemical assays for β-1,3-glucanase or β-1,3-glucan synthase, particularly when performed on fiber cells or the underlying seed coat and particularly when performed immediately prior, during and immediately subsequent to fiber cell elongation, may also be used to identify in a population of cotton plant lines, or a population of cotton relatives which are capable of interbreeding with cotton plant lines, or plant populations resulting from wide crosses between cotton and such cotton relatives or in populations of resynthesized cotton lines, those lines with interesting characteristics, particularly those lines which have a relatively low β-1,3-glucanase activity and/or a relatively high β-1,3-glucan synthase, particularly at the base of fiber cells immediately prior, during and immediately subsequent to the fiber elongation phase.

The following non-limiting Examples describe chimeric genes for the alteration of fiber characteristics in cotton and uses thereof. Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK.

Throughout the description and Examples, reference is made to the following sequences represented in the sequence listing:
SEQ ID No 1: nucleotide sequence of endo-1,3-beta glucanase
SEQ ID No 2: nucleotide sequence of the partial cDNA encoding endo-1,3-β-glucan synthase.
SEQ ID No 3: amino acid sequence encoded by the partial cDNA of SEQ ID No 2.
SEQ ID No 4: amino acid sequence encoded by SEQ ID No 1.

EXAMPLES

Example 1

Figure 1:
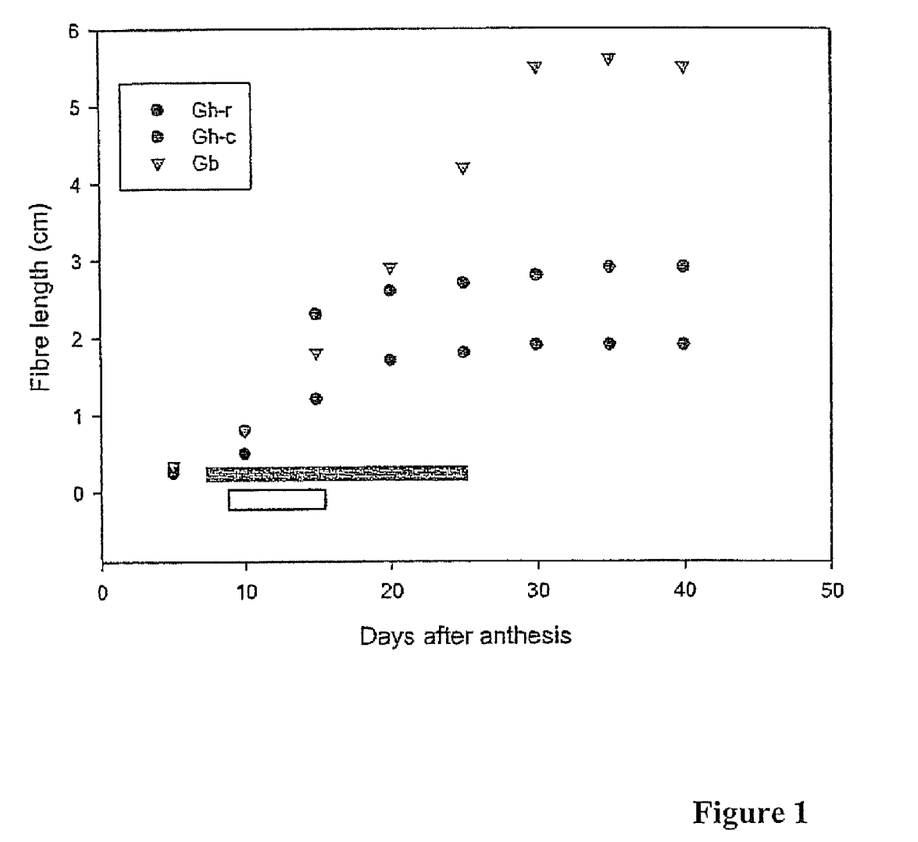
FIG. 1 is a graphic representation of the evolution of the fiber length in time for three tetraploid cotton cultivars with short, normal and long fibers (Gh-r, Gh-c and Gb, respectively). The X-axis represents days after anthesis (DAA), whereas the Y-axis represents the fiber length in cm. The triangles represent the fiber length for Gb, the closed circles represent fiber length for Gh-c and the open circles represent Gh-r. The closure of the plasmodesmata is indicated by the horizontal bars (open bar for Gh-c; closed bar for Gb; plasmodesmata do not close in Gh-r).

Correlation of the Duration of the Closure of the Plasmodesmata with the Length of Fibers, in Different Cotton Cultivars The gating status of fiber plasmodesmata (PD) was examined among three tetraploid cotton cultivars, Gh-r, Gh-c and Gb, with short, normal and long fiber, respectively, by using confocal imaging of a membrane-impermeable fluorescent molecule CF. As summarized in FIG. 1, the genotype Gh-r, with the shortest fiber, does not close its fiber PD. In contrast, the long fiber genotype, Gb, closes PD earlier and longer than the intermediate line (Gh-c). A tetraploid lintless mutant (fls), which produces fuzz-like fiber of less than 0.5 cm, does not close its fiber PD.

It was also found that, among the diploid progenitor of cotton cultivars, an A genome line Ga closes fiber PD for ~10 d and produces about 1.5 cm long fiber, while a D genome line, Gt, does not close PD and virtually no fiber elongation occurs.

These data demonstrate that the genotypic differences in duration of PD closure positively correlate with fiber length.

Example 2

Figure 2:
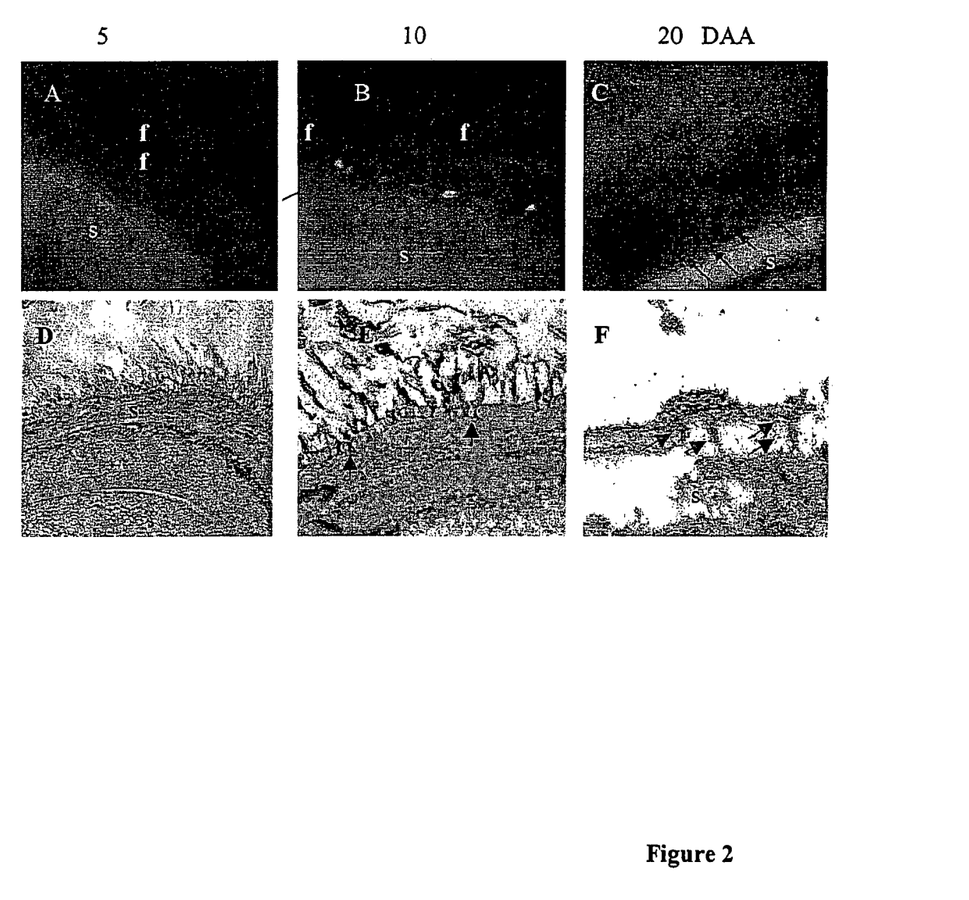
FIG. 2. Localization of callose in plasmodesmata at the fiber base in cultivar Gh-c, at 10 DAA (panels B, E and F) when plasmodesmata were closed, at 5 DAA (panel A and D) before plasmodesmata are closed, or at 20 DAA (panel C) when plasmodesmata are re-opened. Panels A to C: aniline blue fluorescent labeling. Panels D to E: immuno-gold labeling with monoclonal antibody against callose (light-microscope). Panel F: immuno-gold labeling with monoclonal antibody against callose (electron-microscope). Arrows indicate the fiber base, where callose deposition may occur. f: fiber; sc: seed coat.

Analysis of Callose Deposition at the Base of the Fiber Cells in Different Cotton Cultivars The molecular basis of PD gating is virtually unknown. However, callose deposition at the neck region of PD has been shown to close PD in several plant systems. Callose deposition was analyzed using a callose-specific stain, aniline blue. The timing and duration of callose deposition in fiber base, judged from fluorescent signals of aniline blue, matched with that of PD closure in Gh-c and Gb. Representative images from the genotype Gh-c are presented in FIG. 2 (A-C). Callose was undetectable in the fiber base at 5 and 20 DAA when PD were open but became readily detectable at 10 DAA when PD closed (FIG. 2). Similar results were obtained by using antibody against callose. The immuno-gold labelled callose signals were detected at the fiber base at 10 DAA (FIG. 2E), but not at 5 (FIG. 2D) or 20 DAA. At the EM level, callose was localized to the PD at the fiber base (FIG. 2F).

These results show that callose deposition correlates with the closure of fiber PD.

Example 3

Figure 3:
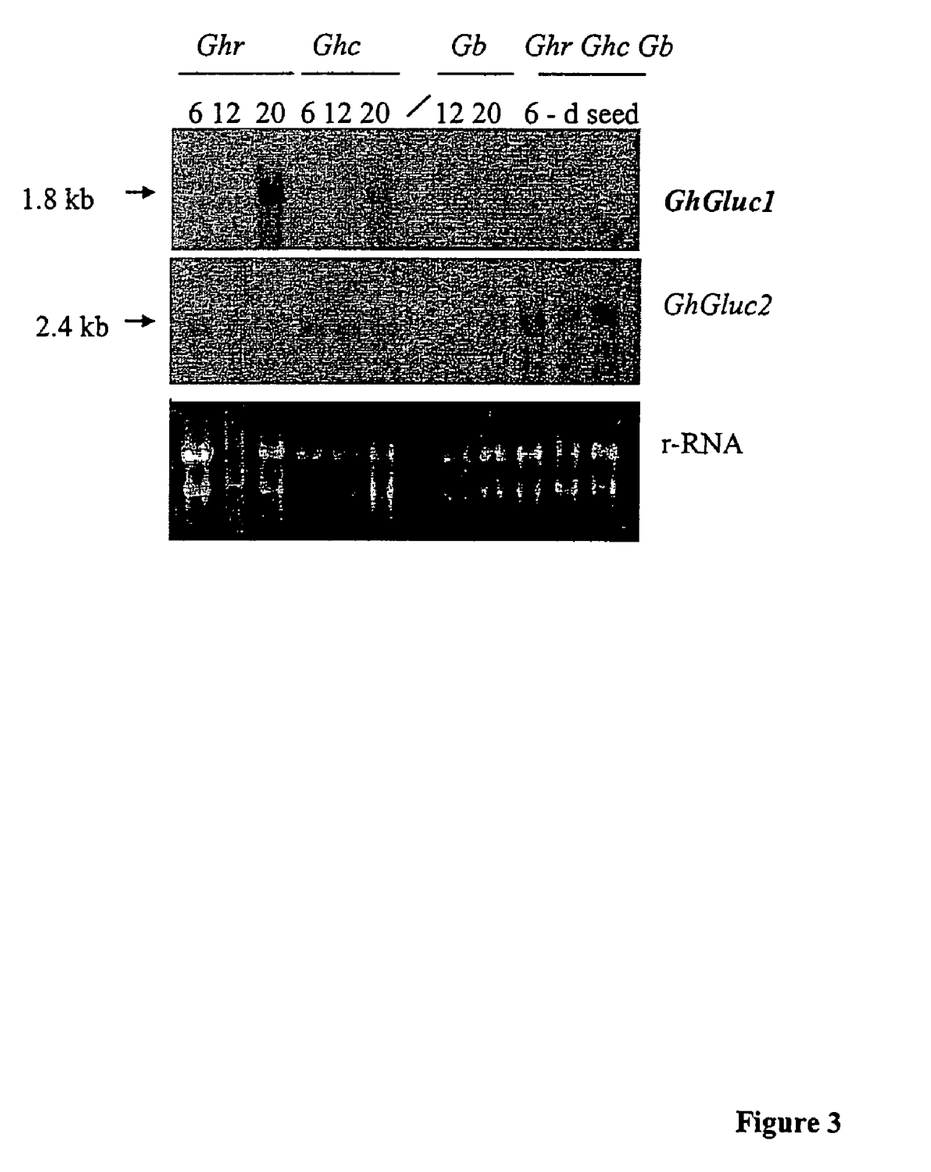
FIG. 3: Northern analysis of mRNA, prepared from developing fibers 6, 12 and 20 DAA and 6-d seed, in Gh-r, Gh-c and Gb cotton cultivars. The used probes are either a cDNA clone of β-1,3 glucanase comprising the sequence of SEQ ID No 1 (upper panel) or a cDNA clone of β-1,3 glucanase comprising the sequence with Accession number A1728205).

Analysis of the expression of a fiber-specific β-1,3-glucanase gene (GhGluc1) in cotton To analyze the role of β-1,3 glucanase in the molecular mechanism of PD closure/re-opening, a partial β-1,3 glucanase cDNA (GhGluc1) from cotton fiber mRNA was cloned (using the sequence information with Genbank accession number D88416). FIG. 3 shows that the mRNA of this gene is expressed only at 20 DAA (matching with the timing of callose disappearance—see FIG. 2 C) and not at 10~12 DAA in Gh-c, when callose was present at the fiber base (see FIGS. 2 B and E). Consistently, the GhGluc1 was not expressed at ~6 DAA (FIG. 3) when callose has not been produced (FIG. 2 A). Significantly, at 20 DAA, the mRNA levels of the gene are strongest, weaker and undetectable in Gh-r, Gh-c and Gb, representing short, intermediate and long fiber cultivars, respectively (FIG. 3). The expression of this gene is fiber specific as its mRNA is undetectable in 6-d young seed (FIG. 3), embryo, shoot or root.

Taken together, the data show that the expression of GhGluc1 is fiber- and developmental-specific. The timing and the level of the GhGluc1 expression among the three cultivars differing in fiber length suggest that GhGluc1 is responsible for the degradation of callose in the PD, which either prevents PD closure (e.g. in Gh-r) or allows PD to re-open (e.g. in Gh-c), hence shortens the elongation period.

Example 4

Increasing Fiber Length by Silencing GhGluc1 Expression in Cotton Fiber

A chimeric gene is constructed containing the following DNA elements:
a CaMV35S promoter
a sense RNA encoding region corresponding to the nucleotide sequence of SEQ ID No 1
a antisense RNA encoding region corresponding to the complement of the nucleotide sequence of SEQ ID No 1.
A 3' nos terminator region
This chimeric gene is introduced into a T-DNA vector together with a selectable bar gene. The T-DNA vector is introduced into *Agrobacterium tumefaciens* and used to produce transgenic cotton plants.

Transgenic cotton plants comprising the chimeric gene are analyzed as in Examples 1 and 2. The fiber elongation phase is prolonged when compared to the untransformed control cotton plants, and the fibers are longer than in the untransformed control cotton plants.

Example 5

Increasing fiber elongation by expression of a chimeric β-1,3 glucan synthase in cotton fiber A chimeric gene is constructed containing the following DNA elements:
a cotton expansin promoter;
a B-1,3 glucan synthase encoding region comprising the nucleotide sequence of SEQ ID No 2;
a 3' nos terminator region.
This chimeric gene is introduced into a T-DNA vector together with a selectable bar gene. The T-DNA vector is introduced into *Agrobacterium tumefaciens* and used to produce transgenic cotton plants.

Transgenic cotton plants comprising the chimeric gene are analyzed as in Examples 1 and 2. The fiber elongation phase is prolonged when compared to the untransformed control cotton plants, and the fibers are longer than in the untransformed control cotton plants.

In summary, the invention relates to the following embodiments:

1. A method for modifying a fiber of a fiber-producing plant comprising the step of altering a fiber cell elongation phase by modulating deposition of callose at the neck of the plasmodesmata at the base of said fiber cell.
2. A method for increasing the length of a fiber of a fiber producing plant, comprising the step of introducing a chimeric gene into a cell of said fiber producing plant, wherein said chimeric gene, when expressed in said cell of said fiber-producing plant increases said deposition of callose and increases said fiber elongation phase.
3. The method according to paragraph 2, wherein said chimeric gene comprises the following operably linked DNA elements:
   (a) a plant expressible promoter, preferably a plant expressible promoter which controls transcription preferentially in said fiber cells;
   (b) a transcribed DNA region, which when transcribed yields a double-stranded RNA molecule capable of reducing the expression of a gene endogenous to said fiber producing plant, said gene being involved in callose removal from said plasmodesmata, and said RNA molecule comprising a first and second RNA region wherein
    i) said first RNA region comprises a nucleotide sequence of at least 19 consecutive nucleotides having at least about 94% sequence identity to the nucleotide sequence of said endogenous gene;
    ii) said second RNA region comprises a nucleotide sequence complementary to said 19 consecutive nucleotides of said first RNA region;
    iii) said first and second RNA region are capable of base-pairing to form a double stranded RNA molecule between at least said 19 consecutive nucleotides of said first and second region; and
    (c) a 3' end region comprising transcription termination and polyadenylation signals functioning in cells of said plant.
4. The method according to paragraph 3, wherein said promoter is a fiber-specific beta tubulin promoter from cotton, a fiber-specific actin promoter from cotton, a fiber specific promoter from a lipid transfer protein gene from cotton, a promoter from an expansin gene from cotton or a promoter from a chitinase gene in cotton.
5. The method according to paragraph 3 or 4, wherein said endogenous gene is a 1,3-β-glucanase gene which is expressed at the base of said fiber cell, at the end of said fiber elongation phase in said fiber producing plant.
6. The method according to paragraph 5, wherein said endogenous gene encodes a protein comprising the amino acid sequence of SEQ ID No 4 or wherein said gene comprises the nucleotide sequence of SEQ ID No 1.
7. The method according to anyone of paragraphs 3 to 6, wherein said first RNA region comprises a nucleotide sequence of at least 19 consecutive nucleotides having at least about 94% sequence identity to a nucleotide sequence encoding a protein comprising the amino acid sequence of SEQ ID No 4 or to the nucleotide sequence of SEQ ID No 1.
8. The method according to paragraph 2, wherein said chimeric gene comprises
    (a) a plant-expressible promoter, preferably a plant-expressible promoter which controls transcription preferentially in said fiber cells;
    (b) a DNA region encoding a β-1,3 glucan synthase protein; and
    (c) a 3'end region comprising transcription termination and polyadenylation signals functioning in cells of said plant.
9. The method according to paragraph 8, wherein said DNA region encoding said β-1,3 glucan synthase protein, comprises the nucleotide sequence of SEQ ID No 2.
10. The method according to paragraph 8 or 9, wherein said promoter is a fiber-specific beta tubulin promoter from cotton, a fiber-specific actin promoter from cotton, a fiber specific promoter from a lipid transfer protein gene from cotton, a promoter from an expansin gene from cotton or a promoter from a chitinase gene in cotton.
11. The method according to any on of paragraphs 2 to 10, wherein said fiber producing plant is cotton.
12. The method according to paragraph 11, wherein said fiber is a lint fiber.
13. The method according to paragraph 11, wherein said fiber is a fuzz fiber.
14. The method according to paragraph 3, further comprising introducing a second chimeric gene, wherein said second chimeric gene comprises the following operably linked DNA fragments:
    (a) a plant-expressible promoter, preferably a plant-expressible promoter which controls transcription preferentially in said fiber cells;
    (b) a DNA region encoding a β-1,3 glucan synthase protein; and
    (c) a 3'end region comprising transcription termination and polyadenylation signals functioning in cells of said plant.
15. The method according to any one of paragraphs 1 to 14, further comprising
    (a) growing plants obtained according to said method; and
    (b) isolating fibers from said fiber-producing plants
16. A method for decreasing the length of a fiber of a fiber producing plant, comprising the step of introducing a chimeric gene into a cell of said fiber producing plant, wherein said chimeric gene, when expressed in said cell of said fiber-producing plant decreases said fiber elongation phase and decreases said deposition of callose.
17. The method according to paragraph 16, wherein said chimeric gene said chimeric gene comprises the following operably linked DNA fragments:
    (a) a plant-expressible promoter, preferably a plant-expressible promoter which controls transcription preferentially in said fiber cells;
    (b) a DNA region encoding a β-1,3 glucanase protein; and
    (c) a 3'end region comprising transcription termination and polyadenylation signals functioning in cells of said plant.
18. The method according to paragraph 17, wherein said DNA region encoding said β-1,3 glucanase protein comprises the nucleotide sequence of SEQ ID No 1.
19. The method according to paragraph 17 or 18, wherein said promoter is a fiber-specific beta tubulin promoter from cotton, a fiber-specific actin promoter from cotton, a fiber specific promoter from a lipid transfer protein gene from cotton, a promoter from an expansin gene from cotton or a promoter from a chitinase gene in cotton.
20. The method according to paragraph 16, wherein said chimeric gene comprises the following operably linked DNA elements:
    (a) a plant expressible promoter which controls transcription preferentially in said fiber cells;
    (b) a transcribed DNA region, which when transcribed yields a double-stranded RNA molecule capable of reducing the expression of a gene endogenous to said fiber producing plant, said gene being involved in callose deposition in said plasmodesmata, and said RNA molecule comprising a first and second RNA region wherein
        i) said first RNA region comprises a nucleotide sequence of at least 19 consecutive nucleotides having at least about 94% sequence identity to the nucleotide sequence of said endogenous gene;
        ii) said second RNA region comprises a nucleotide sequence complementary to said 19 consecutive nucleotides of said first RNA region;
        iii) said first and second RNA region are capable of base-pairing to form a double stranded RNA molecule between at least said 19 consecutive nucleotides of said first and second region; and
    (c) a 3' end region comprising transcription termination and polyadenylation signals functioning in cells of said plant.
21. The method according to paragraph 20, wherein said promoter is a fiber-specific beta tubulin promoter from cotton, a fiber-specific actin promoter from cotton, a fiber specific promoter from a lipid transfer protein gene from cotton, a promoter from an expansin gene from cotton or a promoter from a chitinase gene in cotton.

22. The method according to paragraph 20 or 21, wherein said endogenous gene is a 1,3-β-glucan synthase gene which is expressed in said fiber of said fiber producing plant.

23. The method according to paragraph 22, wherein said endogenous gene encodes a protein comprising the amino acid sequence of SEQ ID No 3 or wherein said endogenous gene comprises the nucleotide sequence of SEQ ID No 2.

24. The method according to anyone of paragraphs 21 to 23, wherein said first RNA region comprises a nucleotide sequence of at least 19 consecutive nucleotides having at least about 94% sequence identity to a nucleotide sequence encoding a protein comprising the amino acid sequence of SEQ ID No 3 or to the nucleotide sequence of SEQ ID No 2.

25. A method for identifying allelic variations of the genes encoding proteins involved in fiber elongation in a population of different genotypes, cultivars or varieties of a particular plant species, preferably a fiber-producing plant species, which are correlated either alone or in combination with the length of fibers produced, comprising the steps of
    (a) providing a population of different varieties or genotypes of a particular plant species or interbreeding plant species comprising different allelic forms of the nucleotide sequences encoding callose synthase or β-1,3 glucanase, particularly of SEQ ID No 1 or SEQ ID 2;
    (b) determining parameters related to fiber length for each individual of the population;
    (c) determining the presence of a particular allelic form of the nucleotide sequences encoding callose synthase or β-1,3 glucanase, particularly of SEQ ID No 1 or SEQ ID 2;
    (d) correlating the occurrence of particular fiber length with the presence of a particular allelic form of the mentioned nucleotide sequence or a particular combination of such allelic forms.

26. A chimeric gene as described in any one of paragraphs 3 to 24.

27. A cell of a fiber-producing plant comprising a chimeric gene according to paragraph 26.

28. A fiber producing plant comprising a chimeric gene according to paragraph 26.

29. A fiber producing plant according to paragraph 28, wherein fibers of said plant are increased in length compared to untransformed control plants.

30. A fiber producing plant according to paragraph 28, which has increased drought resistance.

31. A fiber producing plant according to any one of paragraphs 28 to 30, wherein said plant is cotton.

32. Seed of the fiber producing plant according to any one of paragraphs 26 to 31, said seed comprising a chimeric gene according to paragraph 26.

33. Fibers produced according to the methods of any one of paragraphs 1 to 24.

34. A method for increasing drought resistance in a fiber producing plant, said method comprising
    (a) introducing a chimeric gene into cells of said fiber producing plant wherein said chimeric gene comprises the following operably linked DNA elements:
        i) a plant expressible promoter which controls transcription preferentially in said fiber cells;
        ii) a transcribed DNA region, which when transcribed yields a double-stranded RNA molecule capable of reducing the expression of a gene endogenous to said fiber producing plant, said gene being involved in callose removal in said plasmodesmata, and said RNA molecule comprising a first and second RNA region wherein
            (1) said first RNA region comprises a nucleotide sequence of at least 19 consecutive nucleotides having at least about 94% sequence identity to the nucleotide sequence of said endogenous gene;
            (2) said second RNA region comprises a nucleotide sequence complementary to said 19 consecutive nucleotides of said first RNA region;
            (3) said first and second RNA region are capable of base-pairing to form a double stranded RNA molecule between at least said 19 consecutive nucleotides of said first and second region; and
        iii) a 3' end region comprising transcription termination and polyadenylation signals functioning in cells of said plant.

We claim:

1. A method for increasing the length of a fiber in cotton, comprising introducing a chimeric gene in a fiber cell of a cotton plant, wherein said chimeric gene, when expressed in said cell of said cotton plant increases a fiber elongation phase and increases deposition of callose, said chimeric gene comprising the following operably linked DNA elements:
   i) a plant-expressible promoter which controls transcription preferentially in said fiber cells;
   ii) a DNA region encoding a beta-1,3 glucan synthase protein; and
   iii) a 3'end region comprising transcription termination and polyadenylation signals functioning in cells of said cotton plant.

2. A method according to claim 1 wherein said DNA region encodes a beta-1,3-glucan synthase comprising the amino acid sequence encoded by GenBank Accession No. AF085717 or said DNA region comprises the nucleotide sequence of GenBank Accession No. AF085717.

3. A method according to claim 1 wherein said plant-expressible promoter is a fiber-specific beta tubulin promoter from cotton, a fiber-specific actin promoter from cotton, a fiber specific promoter from a lipid transfer protein gene from cotton, a promoter from an expansin gene from cotton or a promoter from a chitinase gene in cotton.

4. A method according to claim 3 wherein said fiber is a lint or a fuzz fiber.

5. A method according to claim 4 wherein said method further comprises iv) growing plants obtained according to said method; and v) isolating fibers from said cotton plants.

6. A cell of a cotton plant comprising a chimeric gene comprising the three operably linked DNA elements i), ii) and iii) as recited in claim 1.

7. A cell of a cotton plant comprising a chimeric gene comprising the three operably linked DNA elements i), ii) and iii) as recited in claim 2.

8. A cell of a cotton plant comprising a chimeric gene comprising the three operably linked DNA elements i), ii) and iii) as recited in claim 3.

9. A cotton plant comprising a chimeric gene comprising the three operably linked DNA elements i), ii) and iii) as recited in claim 1.

10. A cotton plant comprising a chimeric gene comprising the three operably linked DNA elements i), ii) and iii) as recited in claim 2.

11. A cotton plant comprising a chimeric gene comprising the three operably linked DNA elements i), ii) and iii) as recited in claim 3.

12. Seed of a cotton plant, said seed comprising a chimeric gene comprising the three operably linked DNA elements i), ii) and iii) as recited in claim 1.

13. Seed of a cotton plant, said seed comprising a chimeric gene comprising the three operably linked DNA elements i), ii) and iii) as recited in claim 2.

14. Seed of a cotton plant, said seed comprising a chimeric gene comprising the three operably linked DNA elements i), ii) and iii) as recited in claim 3.

* * * * *

SEQUENCE LISTING

```
<160> NUMBER OF SEQ ID NOS: 4

<210> SEQ ID NO 1
<211> LENGTH: 800
<212> TYPE: DNA
<213> ORGANISM: Gossypium hirsutum
<220> FEATURE:
<221> NAME/KEY: misc_feature
<222> LOCATION: (726)..(726)
<223> OTHER INFORMATION: n =any nucleotide
<220> FEATURE:
<221> NAME/KEY: misc_feature
<222> LOCATION: (789)..(789)
<223> OTHER INFORMATION: n =any nucleotide

<400> SEQUENCE: 1
attttctggg tttttaatct cagcaatggt gtttttaact caactcctct ctctaacaga      60
tggccgtgat attggtgttt gctatggttt gaacggcaac aatcttccat ctccaggaga     120
tgttattaat ctttacaaaa ctagtggcat aaacaatatc aggctctacc agccttaccc     180
tgaagtgctc gaagcagcaa ggggatcggg aatatccctc tcgatgggtc cgagaaacga     240
```

```
ggacatacaa agcctcgcaa aagatcaaag tgcagccgat gcatgggtta acaccaacat     300
cgtcccttat aaggacgatg ttcagttcaa gttgatcact attgggaatg aagccatttc     360
aggacaatca agctcttaca ttcctgatgc catgaacaac ataatgaact cgctcgcctt     420
atttgggtta ggcacgacga aggttacgac cgtggtcccg atgaatgccc taagtacctc     480
gtaccctcct tcagacggcg cttttggaag cgatataaca tcgatcatga ctagtatcat     540
ggccattctg gctgtacagg attcgcccct cctgatcaat gtgtacccct attttgccta     600
tgcctcagac cccactcata tttccctcga ttacgccttg ttcacctcga ccgcaccggt     660
ggtggtcgac caaggcttgg aatactacaa cctctttgac ggcatggtcg atgctttcaa     720
tgccgnccta gataagatcg gcttcggcca aattactctc attgtagccg aaactggatg     780
gccgaccgnc ggtaacgagc                                                 800
```

```
<210> SEQ ID NO 2
<211> LENGTH: 602
<212> TYPE: DNA
<213> ORGANISM: Gossypium hirsutum
<220> FEATURE:
<221> NAME/KEY: CDS
<222> LOCATION: (2)..(601)

<400> SEQUENCE: 2 a tat att ttc ctt tat gga agg gct tat ttg gca ctt tct gga gtt ggt       49
  Tyr Ile Phe Leu Tyr Gly Arg Ala Tyr Leu Ala Leu Ser Gly Val Gly
  1               5                   10                  15 gaa aca atg caa gta aaa gct cgg ata aca gat aac gcc gct ctt gaa        97
Glu Thr Met Gln Val Lys Ala Arg Ile Thr Asp Asn Ala Ala Leu Glu
            20                  25                  30 gct gct cta aat act cag ttt ctg ttt caa att ggt atc ttt tca gct       145
Ala Ala Leu Asn Thr Gln Phe Leu Phe Gln Ile Gly Ile Phe Ser Ala
        35                  40                  45 gtg cca atg gtt ttg ggc ttc atc ttg gag caa ggt ttc cta agg gct       193
Val Pro Met Val Leu Gly Phe Ile Leu Glu Gln Gly Phe Leu Arg Ala
    50                  55                  60 att gtc agt ttt att aca atg cag tta cag ctt tgt act gtt ttc ttc       241
Ile Val Ser Phe Ile Thr Met Gln Leu Gln Leu Cys Thr Val Phe Phe
65                  70                  75                  80 aca ttc tcc ctg ggt aca aga act cat tat ttt ggt cgg aca atc ctg       289
Thr Phe Ser Leu Gly Thr Arg Thr His Tyr Phe Gly Arg Thr Ile Leu
                85                  90                  95 cat ggt ggt gca agg tat caa gct aca ggt aga ggt ttt gtg gtc cgc       337
His Gly Gly Ala Arg Tyr Gln Ala Thr Gly Arg Gly Phe Val Val Arg
            100                 105                 110 cat att aaa ttt tct gag aac tac aga ctg tat tct cgc agt cat ttt       385
His Ile Lys Phe Ser Glu Asn Tyr Arg Leu Tyr Ser Arg Ser His Phe
        115                 120                 125 gtt aaa ggg cta gaa gtt gtg ctt ctg ttg gtg gta tac ctt gca tat       433
Val Lys Gly Leu Glu Val Val Leu Leu Leu Val Val Tyr Leu Ala Tyr
    130                 135                 140 ggg tat aat gat agt gca ttg tcg tac att ctt cta tca att agc agt       481
Gly Tyr Asn Asp Ser Ala Leu Ser Tyr Ile Leu Leu Ser Ile Ser Ser
145                 150                 155                 160 tgg ttt atg gct ctt tca tgg ctt ttc gca ccc tat ttg ttc aat cct       529
Trp Phe Met Ala Leu Ser Trp Leu Phe Ala Pro Tyr Leu Phe Asn Pro
                165                 170                 175 tct gga ttt gag tgg caa aag att gtg gat gat ttc aaa gat tgg aca       577
Ser Gly Phe Glu Trp Gln Lys Ile Val Asp Asp Phe Lys Asp Trp Thr
            180                 185                 190
```

```
                aat tgg cta ttt tac aga ggc gga c                              602
                Asn Trp Leu Phe Tyr Arg Gly Gly
                        195                 200

<210> SEQ ID NO 3
<211> LENGTH: 200
<212> TYPE: PRT
<213> ORGANISM: Gossypium hirsutum

<400> SEQUENCE: 3

Tyr Ile Phe Leu Tyr Gly Arg Ala Tyr Leu Ala Leu Ser Gly Val Gly
1               5                   10                  15

Glu Thr Met Gln Val Lys Ala Arg Ile Thr Asp Asn Ala Ala Leu Glu
            20                  25                  30

Ala Ala Leu Asn Thr Gln Phe Leu Phe Gln Ile Gly Ile Phe Ser Ala
        35                  40                  45

Val Pro Met Val Leu Gly Phe Ile Leu Glu Gln Gly Phe Leu Arg Ala
    50                  55                  60

Ile Val Ser Phe Ile Thr Met Gln Leu Gln Leu Cys Thr Val Phe Phe
65                  70                  75                  80

Thr Phe Ser Leu Gly Thr Arg Thr His Tyr Phe Gly Arg Thr Ile Leu
                85                  90                  95

His Gly Gly Ala Arg Tyr Gln Ala Thr Gly Arg Gly Phe Val Val Arg
            100                 105                 110

His Ile Lys Phe Ser Glu Asn Tyr Arg Leu Tyr Ser Arg Ser His Phe
        115                 120                 125

Val Lys Gly Leu Glu Val Val Leu Leu Val Val Tyr Leu Ala Tyr
    130                 135                 140

Gly Tyr Asn Asp Ser Ala Leu Ser Tyr Ile Leu Leu Ser Ile Ser Ser
145                 150                 155                 160

Trp Phe Met Ala Leu Ser Trp Leu Phe Ala Pro Tyr Leu Phe Asn Pro
                165                 170                 175

Ser Gly Phe Glu Trp Gln Lys Ile Val Asp Asp Phe Lys Asp Trp Thr
            180                 185                 190

Asn Trp Leu Phe Tyr Arg Gly Gly
        195                 200

<210> SEQ ID NO 4
<211> LENGTH: 241
<212> TYPE: PRT
<213> ORGANISM: Artificial
<220> FEATURE:
<223> OTHER INFORMATION: amino acid sequence encoded by the partial
      cDNA of SEQ ID No 1

<400> SEQUENCE: 4

Phe Ser Gly Phe Leu Ile Ser Ala Met Val Phe Leu Thr Gln Leu Leu
1               5                   10                  15

Ser Leu Thr Asp Gly Arg Asp Ile Gly Val Cys Tyr Gly Leu Asn Gly
            20                  25                  30

Asn Asn Leu Pro Ser Pro Gly Asp Val Ile Asn Leu Tyr Lys Thr Ser
        35                  40                  45

Gly Ile Asn Asn Ile Arg Leu Tyr Gln Pro Tyr Pro Glu Val Leu Glu
    50                  55                  60

Ala Ala Arg Gly Ser Gly Ile Ser Leu Ser Met Gly Pro Arg Asn Glu
65                  70                  75                  80

Asp Ile Gln Ser Leu Ala Lys Asp Gln Ser Ala Ala Asp Ala Trp Val
                85                  90                  95
```

-continued

```
Asn Thr Asn Ile Val Pro Tyr Lys Asp Asp Val Gln Phe Lys Leu Ile
            100             105             110

Thr Ile Gly Asn Glu Ala Ile Ser Gly Gln Ser Ser Ser Tyr Ile Pro
        115             120             125

Asp Ala Met Asn Asn Ile Met Asn Ser Leu Ala Leu Phe Gly Leu Gly
        130             135             140

Thr Thr Lys Val Thr Thr Val Val Pro Met Asn Ala Leu Ser Thr Ser
145             150             155             160

Tyr Pro Pro Ser Asp Gly Ala Phe Gly Ser Asp Ile Thr Ser Ile Met
                165             170             175

Thr Ser Ile Met Ala Ile Leu Ala Val Gln Asp Ser Pro Leu Leu Ile
            180             185             190

Asn Val Tyr Pro Tyr Phe Ala Tyr Ala Ser Asp Pro Thr His Ile Ser
        195             200             205

Leu Asp Tyr Ala Leu Phe Thr Ser Thr Ala Pro Val Val Val Asp Gln
        210             215             220

Gly Leu Glu Tyr Tyr Asn Leu Phe Asp Gly Met Val Asp Ala Phe Asn
225             230             235             240

Ala
```